United States Patent

Furihata et al.

[11] Patent Number: 5,840,944
[45] Date of Patent: Nov. 24, 1998

[54] METHOD TO PRODUCE HIGHLY PURE EICOSAPENTAENOIC ACID OR ITS ESTER

[75] Inventors: Kiyomi Furihata; Kazuhiko Hata, both of Tokyo, Japan

[73] Assignee: Nippon Suisan Kaisha, Ltd., Tokyo, Japan

[21] Appl. No.: 232,021
[22] PCT Filed: Oct. 28, 1992
[86] PCT No.: PCT/JP92/01393
  § 371 Date: Jun. 27, 1994
  § 102(e) Date: Jun. 27, 1994
[87] PCT Pub. No.: WO93/09210
  PCT Pub. Date: May 13, 1993

[30] Foreign Application Priority Data

Oct. 28, 1991 [JP] Japan ................................. 3-281686

[51] Int. Cl.$^6$ ....................................................... C11B 3/12
[52] U.S. Cl. .................... 554/175; 554/191; 554/193; 202/41; 202/81; 202/82; 202/98
[58] Field of Search ................................... 554/178, 186, 554/191, 193; 203/98, 82, 41, 81

[56] References Cited

U.S. PATENT DOCUMENTS 5,215,630   6/1993   Hata et al. .................................. 203/38

FOREIGN PATENT DOCUMENTS

| 57-149400 | 9/1982 | Japan . |
| 58-8037 | 1/1983 | Japan . |
| 58-88339 | 5/1983 | Japan . |
| 60-208940 | 10/1985 | Japan . |

Primary Examiner—Gary Geist
Assistant Examiner—Deborah D Carr
Attorney, Agent, or Firm—Wenderoth, Lind & Ponack, L.L.P.

[57] ABSTRACT

A mixture of fatty acids or their esters derived from natural oils and fats including eicosapentaenoic acids or their derivatives is precision distilled under a high vacuum using a plurality of distillation columns, three distillation columns or more in particular, in order to acquire a fraction consisting mainly of fatty acids of carbon number 20 or their esters, which is then subjected to a column chromatography with a reversed-phase distribution system. Eicosapentaenoic acids or their esters, which is useful for preventing or treating thrombus, with a purity as high as 99% and above and with a recovery rate 55% or above, is produced.

5 Claims, 2 Drawing Sheets

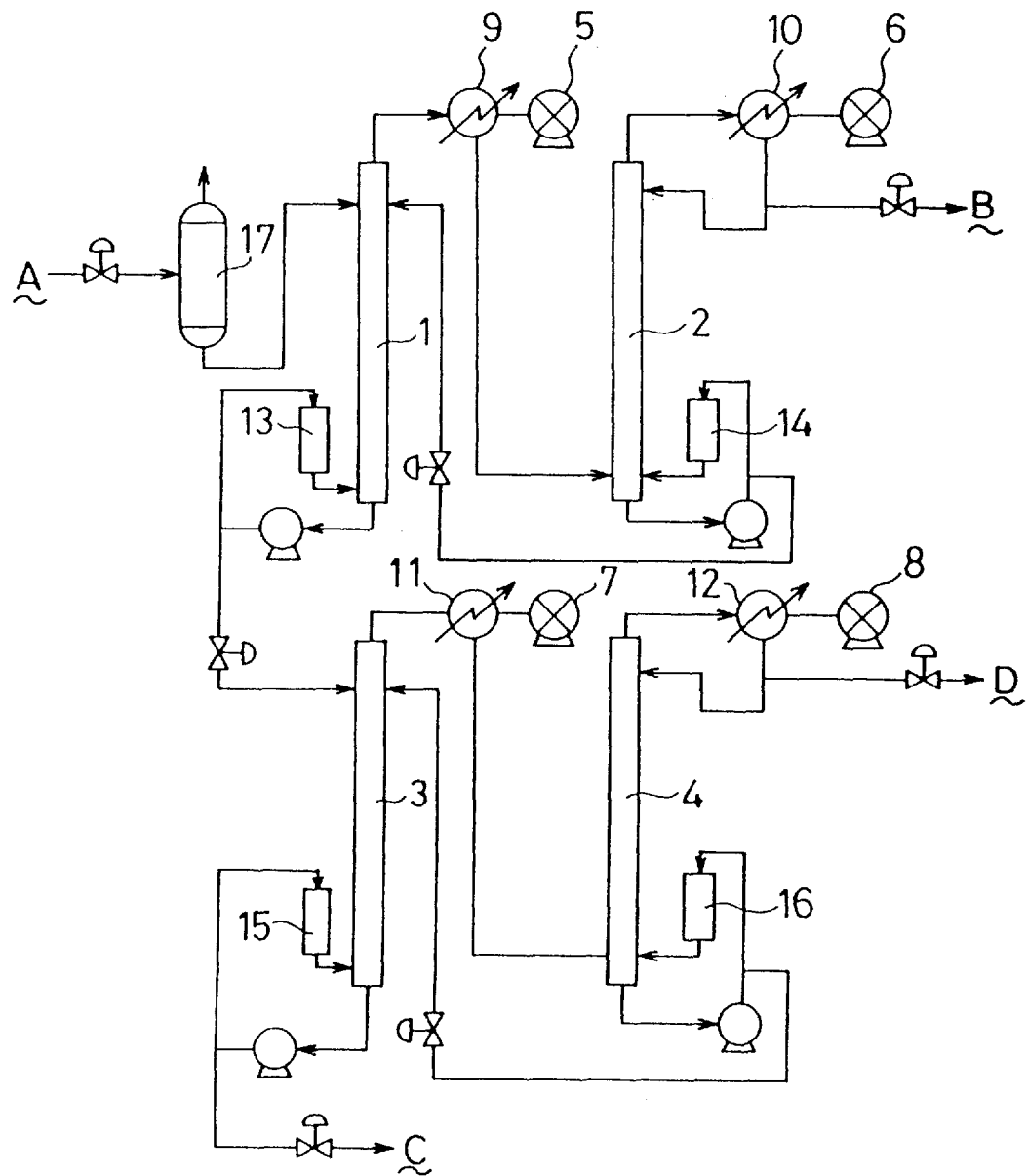

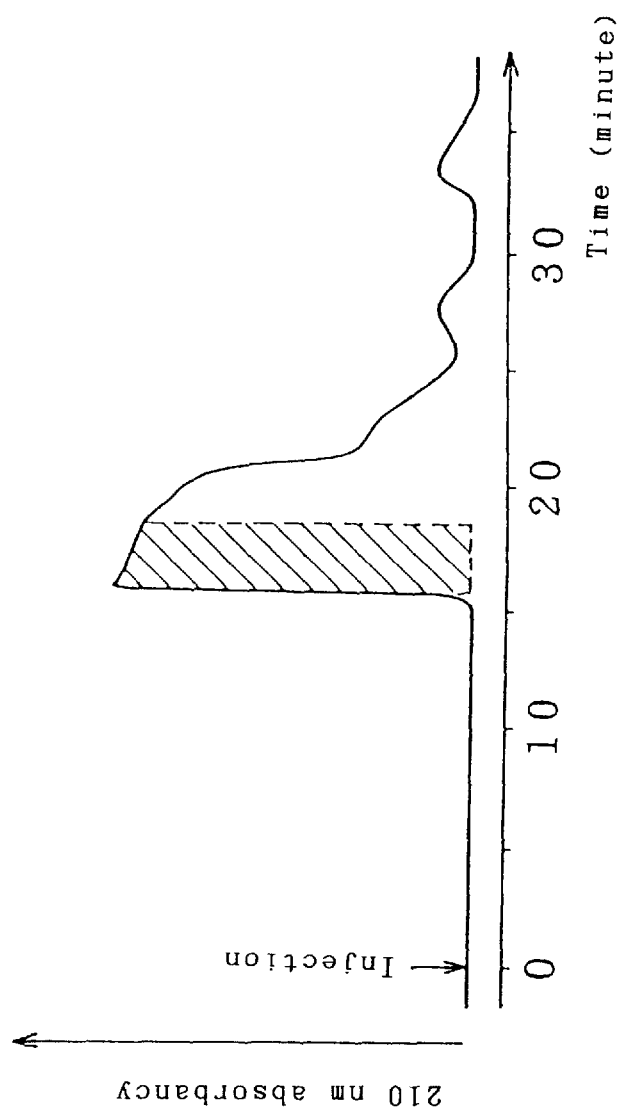

METHOD TO PRODUCE HIGHLY PURE EICOSAPENTAENOIC ACID OR ITS ESTER

This application is a 371 of PCT/JP92/01393 filed Oct. 28, 1992.

TECHNICAL FIELD

The present invention relates to a method of producing highly pure eicosapentaenoic acids or their esters. More particularly, the present invention relates to a novel, highly efficient method of producing highly pure eicosapentaenoic acids (EPA) or their esters, which is a useful in the treatment and prevention of thrombotic diseases.

BACKGROUND TECHNOLOGY

It is well known for many years that eicosapentaenoic acids (EPA), their esters, amides and the like are useful for the prevention of thrombus and the treatment of thrombotic disease.

It is also well known that these eicosapentaenoic acids occur in natural and aquatic oils and fats, such as in mackerels, sardines, and cods, in particular, per se or as derivatives such as glycerides. Many published papers propose a method to separate eicosapentaenoic acids from these fish oils and the like.

Natural fats consisting of these fish oils, however, contain, in addition to eicosapentaenoic acids of carbon number 20 and double bond number 5, an overwhelmingly large quantity of diverse fatty acids with carbon numbers ranging from 12 to 24, and double bond numbers from 0 to 6. It is thus very difficult to effectively isolate and refine eicosapentaenoic acids as a pure product of a high concentration.

As one of the methods to isolate and refine eicosapentaenoic acids, a method to rectifying a mixture of fatty acids containing eicosapentaenoic acids and then refining them by forming urea adducts is known (publication of unexamined patent application Nos. 149400-1982 and 8037-1983). With this method, however, eicosapentaenoic acids are only insufficiently isolated from other C20 high level unsaturated fatty acids and intervening C18 and C22 high level unsaturated fatty acids, with the result that only 95% pure products are produced at best. In fact, the method disclosed in unexamined patent application No. 149400 indicates that a 93.5% purity is the highest achievable level in its working example 3. EPA recovery is also a very low 30%.

The use of reversed-phase partition type column chromatography is proposed as a means to partition-refine eicosapentaenoic acids (publication of unexamined patent application No. 88339-1983). With this method, however, in spite of using raw materials containing highly concentrated (30%) eicosapentaenoic acids, the same quantity of docosahexaenoic acids (DHA) are included in the final product, and these two are only incompletely separated, with the result that the yield of 95% pure eicosapentaenoic acids is only 40%.

It is thus very difficult with conventional methods to produce highly pure eicosapentaenoic acids, those of 95% purity and above in particular, from a mixture of fats with a high recovery rate.

DISCLOSURE OF THE PRESENT INVENTION

The present invention has been made in view of the above circumstances to provide a novel method, by eliminating the drawbacks of conventional methods, to produce highly pure eicosapentaenoic acids or their esters with a high recovery rate, which is also available for acquiring products which are 95% pure or above.

To solve the problems encountered in conventional methods, the present invention provides a method to produce highly pure eicosapentaenoic acids or their esters wherein a mixture of fatty acids or their ester produced from natural oils and fats containing eicosapentaenoic acids or their derivatives is precision distilled under a high vacuum using a plurality of distillation columns to derive a fraction mainly comprising fatty acids of carbon number 20 or their esters, which is then subjected to a reversed-phase partition type column chromatography for partition refinement.

BRIEF DESCRIPTION OF THE DRAWINGS

FIG. 1 shows the structure of a continuous distillation method used in the present invention.

FIG. 2 is the absorbency spectrum of a chromatography as a working example of the present invention.

DETAILED DESCRIPTION OF THE PRESENT INVENTION

The key points of the present invention are removal to the extent possible of fatty acids other than C20 fatty acids by aligning the carbon number of fatty acids or their esters through high level multi-column rectification using a plurality of distillation columns of a high separating power, followed by partition refining by means of the above-mentioned reversed-phase partition type column chromatography, thereby producing eicosapentaenoic acids or their ester of a super high purity of 95% and above, 99% and above in particular, in the industrial production achieving a dramatically increased recovery rate.

It is totally impossible with conventional methods to acquire products of such a high purity with a high recovery rate, and the possibility has never been envisaged. More specifically, long-chain high level unsaturated fatty acids such as eicosapentaenoic acids have a great number of double bonds in the molecule, and thus deterioration, polymerization and other thermal degeneration occur easily, making it extremely difficult to concentrate them by distillation. Additionally, natural oils and fats containing eicosapentaenoic acids contain various other fatty acids whose boiling points are close to each other, so that it is impossible to separate eicosapentaenoic acids from other fatty acids unless the height of the distillation column and the quantity of reflux are increased considerably. This results in the increased column bottoms pressure and thermal degeneration due to the resultant temperature rise, eventually making it extremely difficult to refine eicosapentaenoic acids by distillation. This exemplifies that it is extremely difficult to acquire eicosapentaenoic acids sufficiently selectively as high level unsaturated long-chain fatty acids from a mixture of fats containing eicosapentaenoic acids.

With the present invention, as described above, rectification is carried out under a high vacuum using a plurality of distillation columns. More specifically, the method is executed using more than one column. Preferably, a mixture of natural oils and fats containing eicosapentaenoic acids or their ester is introduced into three or more distillation columns, one out of which is an independent rectifying column for the initial fraction consisting of fatty acids of a low carbon number: the bottoms liquids of these distillation columns are returned to respective distillation columns one stage before; and distillation is carried out continuously under a reduced pressure of 10 Torr or below and at a bottoms temperature of 210° C. or below.

Desirable embodiments include, in the above continuous distillation, a feed of condensate liquids in the overhead fraction in the distillation column one stage before into the above-mentioned rectifying column assigned to the initial fraction, and provision of two independent rectifying columns for main fraction containing eicosapentaenoic acids and their ester as major components and for after-fraction (residue), respectively, for sustaining continuous operation.

Another desirable embodiment of the present method is provision of an independent vacuum and an condensate system for each distillation column.

The continuous distillation method according to the present invention may be a packed, spring or shelf type, but is not limited thereto. Preferably, a sieve plate may be used and the number of theoretical plates may be five or more.

The continuous distillation column used in the present method can be realized under a reduced pressure of 10 Torr or less, preferably about 0.1 Torr, and with the bottoms temperature at 210° C. or less, preferably 195° C. or less.

In the case where three or more distillation columns are used, one column is exclusively used as a rectifying column for recovering initial fraction. For example, when three columns are used, the columns are classified as follows:
(I) First distillation column
(II) Second distillation column (rectifying column for initial fraction)
(III) Third distillation column (rectifying column for main and after-fraction)

Four columns, when used, are classified as follows:
(I) First distillation column
(II) Second distillation column (rectifying column for initial fraction)
(III) Third distillation column (rectifying column for after-fraction)
(IV) Fourth distillation column (rectifying column for main fraction)

It is also possible to classify as follows when three columns are used:
(I) First distillation column (rectifying column for initial fraction)
(II) Second distillation column (rectifying column for after-fraction)
(III) Third distillation column (rectifying column for main fraction)

It is of course possible to classify the rectifying columns to be used more minutely.

In any case in the present method, the bottoms liquids in the rectifying column for initial fraction are returned as a reflux to the distillation column one stage before, or the first distillation column in the above examples. It is preferable that each column has an exclusive and independent vacuum system because the overhead fraction in the first distillation column is condensed and then fed to the rectifying column for initial fraction in the form of condensate liquid and, further, the vacuum level and bottoms temperature must be strictly controlled in each distillation column.

The present continuous distillation method is described in more detail referring to the attached drawings. The example shown in FIG. 1 in which four distillation columns are used, a mixture of fatty acids or their ester (A) is continuously distilled in four distillation columns (1) through (4).

Each distillation column (1), (2), (3) or (4) is provided with an independent vacuum system (5), (6), (7) or (8), a condensing system (9), (10) or (12), and a reboiler (13), (14), (15) or (16).

Distillation columns (1) through (4) are strictly controlled at a reduced pressure of 1 Torr or below, and at a bottoms temperature of 200° C. or below. Vacuum level and temperature are closely related to each other and hence it is preferable to provide an independent vacuum system for each distillation column, but it is not necessarily essential to provide vacuum systems (5) through (8) which are completely independent from each other for the purpose of the above control. The vacuum system may be suitably constructed according to the capacity of vacuum pumps and control systems to be used, etc.

In the above structure, raw materials (A) are fed to the first distillation column (1), near the overhead, for example. The overhead fraction is condensed in the condensing system (9) and fed to the second distillation column (2) serving as a rectifying column for the initial fraction, at its bottoms, for example. Introduction of the material in the form of liquid is an important factor.

In the second distillation column (2), initial fraction (B) consisting of fatty acids of a low carbon number (<C10) is withdrawn from the overhead. A part of the bottoms liquids is returned to the first distillation column (1) at the overhead or its vicinity. This is another important feature of the method according to the present invention. Bottoms condensate liquids in the first distillation column (1) are heated in the reboiler (13) and returned to the bottoms of the column while introduced into the third distillation column (3) at the overhead or its vicinity in the form of liquid.

Overhead components in the third distillation column (3) are supplied as condensate liquids to the fourth distillation column (4) at the bottoms via the condensing system (11). Bottoms condensate liquids are heated in the reboiler (15) and returned to the bottoms while after-fraction (residue) (C) consisting mainly of longer-chain fatty acids of C21 and above than eicosapentaenoic acids or their ester is recovered.

The overhead (distilled) components in the fourth distillation column (4), supplied with condensate liquids from the overhead of the third distillation column (3), are condensed in the condensing system (12), and a part of the product is returned to the overhead or its vicinity while the main fraction (D) consisting mainly of eicosapentaenoic acids or their ester are recovered. Bottoms condensate liquids are heated in the reboiler (16) and returned to the bottoms while partly returned to the third distillation column (3) at its overhead or its vicinity.

Raw materials (A) may be pre-treated in a flash tank (17) kept at a reduced pressure before they are introduced to the first distillation column (1) to remove air, moisture and other impurities. It is also favorable to use a falling-film evaporation type reboiler for reboilers (13) through (16), in order to shorten heating time. The use of a falling-film evaporation type reboiler is effective for preventing thermal deterioration as well.

The above continuous distillation method avoids the problems encountered in conventional methods described above, and enables production of highly pure eicosapentaenoic acids or their ester of a high concentration of 80% and above with a high efficiency and by simple operation using only the distillation process for refining.

The mixture of fatty acids or their esters to be processed may be arbitrarily obtained from natural oils and fats containing a large quantity of eicosapentaenoic acids or their glycerides and other derivatives, such as a mixture of fatty acids or their esters obtained from suitable items such as sardine, mackerel, herring, mackerel pike and other, fish and marine zooplankton.

When desired, the mixture of these fatty acids is esterified for continuous distillation.

In the present invention, materials are introduced to a reversed-phase partition type column chromatography for partition refining after the above continuous distillation. In this particular case, alkyl bond silica packing materials or the like, for example, is used in columns in order to construct a so-called reversed-phase distribution system. Water, alcohol, ketone or the like may conveniently be used as the solvent system. These materials are used independently or mixed.

Possible pre-processes for the above chromatography include removal of low level unsaturated fatty acids or ester by means of urea addition, low temperature separation and the like.

Production efficiency is further improved in the chromatography by removing beforehand those components which can easily be separated from eicosapentaenoic acids or by carrying out other suitable operations for the multi-column system.

Through partition refining with the column chromatography in this reversed-phase distribution system, the present invention enables acquisition of eicosapentaenoic acids or their ester of 99% purity and above at a 55% recovery rate and above.

The production method according to the present invention is described in more detail referring to working examples below.

Working Example 1

Ethyl ester of a mixture of fatty acids derived from fish oil with the following composition was rectified in a four-column type rectifying system shown in FIG. 1.

|  |  |
|---|---|
| C10 and below | 60% |
| C20 | 23% |
| (of which EPA | 16.5%) |
| C21 and above | 17% |

More specifically, the above ethyl ester mixture was processed in a flash tank (17) kept at 1 Torr vacuum, and supplied to the first distillation column (1), 300 mm in diameter and approximately 7 meters high, kept at 0.1 Torr vacuum at a rate of 16.4 kg/h.

Bottoms temperature was controlled at 195° C. or below, or more concretely at 193° to 195° C., in the first distillation column (1). The number of theoretical plates was four. Vacuum level and temperature at the bottoms of the first distillation column (1) were difficult to control because a mixture of fatty acid ester of C20 and above was easily accumulated at the bottoms. To solve the problem, a smaller quantity of packing materials were used in the first distillation column then they were used in the second distillation column (2).

Overhead condensate liquids in the first distillation column (1) were introduced into the second distillation column (2) at the bottoms. Bottoms temperature in the second column was controlled at 184° to 185° C. The column was operated under a reduced pressure of 0.1 Torr. The number of theoretical plates was six. The overhead fraction was returned at a reflux ratio of 1:2. A part of the overhead fraction was recovered at the rate of 9.9 kg/hr as the initial fraction (B).

The initial fraction was composed of 99% fatty acids of C10 and below, 1% C20 eicosapentaenoic acid ester, etc. and 0% fatty acids of C21 and above.

In the second distillation column (2), the bottoms liquids were controlled at a constant liquid level, and returned to the first distillation column (1) at the overhead or its vicinity. This means that said bottoms condensate liquids were returned to the first reflux column (1) as a reflux. Bottoms liquids in the first distillation column (1) were supplied to the third distillation column (3) at the overhead or its vicinity. The pressure at this time was a reduced pressure of 0.1 Torr and the bottoms temperature was controlled at 195° C. or below in like manner. The number of theoretical plates was four.

Bottoms liquids in the third distillation column (3) were recovered as post-fraction (residue) (C). The post-fraction was composed of 0.1% fatty acid C10 and below, 18% C20 eicosapentaenoic acid ester, etc., and 81.9% fatty acids C21 and above.

Overhead fraction in the third distillation column (3) was supplied to the fourth distillation column at the bottoms as condensate liquids. The fourth distillation column (4) had six theoretical plates, and was operated under a reduced pressure of 0.1 Torr and at a bottoms temperature of 195° C. or below.

The bottoms liquids were returned to the third distillation column (3) at the overhead as a reflux. In this case, the bottoms liquids in the fourth distillation column were controlled at a constant liquid level.

The overhead condensate liquids were returned at a reflux ratio of 1:2 while the main fraction (D) was recovered at a rate of 2.3 kg/h.

The main fraction was composed of 0.1% fatty acids C19 and below, 0% fatty acids C21 and above, and 99.9% C20 eicosapentaenoic acid ester, etc.

Concentration of eicosapentaenoic acid ethyl ester was 82.77% as shown in Table 1.

TABLE 1

| Ca:b ester composition (a and b indicate carbon number and double bond number, respectively) | |
|---|---|
| C18:1 ethyl ester | 0.09% |
| C20:1 ethyl ester | 7.83% |
| C20:4 ethyl ester | 9.01% |
| Eicosapentaenoic acid ethyl ester | 82.77% |
| Other C20 ethyl ester | 0.30% |

Working Example 2

Main fraction produced in Working Example 1 was subjected to high speed liquid column chromatography. Five grams of main fraction was injected into a column which was a stainless steel tube 5 cm in diameter and 50 cm long packed with octadecyl silica gel of particle size 10 to 20 um and eluted with ethanol of liquid quantity of 75 mi/min. The detection was made by 210 nm absorption. The resultant chromatogram is shown in FIG. 2. An eluate from the area corresponding to the hatched area was picked and the solvent was removed under a reduced pressure with a rotary evaporator to produce 3.55 g clear and colorless oily substance. The substance consisted of 99.47% eicosapentaenoic acid ethyl ester and 0.54% C20:4 ethyl ester. The recovery rate for eicosapentaenoic acid ethyl ester in this process was 85.3%. In contrast, the recovery rate for eicosapentaenoic acid ethyl ester from the mixed ethyl ester, the raw material used in Working Example 1, was 60%.

Working Example 3

Methanol in Working Example 2 was substituted with a solvent of 50:50 methanol:acetone for chromatography partition.

As a result, eicosapentaenoic acid ethyl ester of a purity of 99.56% was produced with 61% recovery rate.

Industrial Field of Utilization

The present invention enables the production of highly pure eicosapentaenoic acids or their ester of a purity of 99% and above, which is useful as a prescription and the like for the treatment and prevention of thrombotic disease, at an excellent recovery rate of 55% and above.

We claim:

1. A method of producing highly pure eicosapentaenoic acids or their ester wherein a mixture of fatty acids or their esters derived from natural oils and fats containing eicosapentaenoic acids or their derivatives is precision distilled in a plurality of distillation columns under a high vacuum to acquire a fraction consisting mainly of fatty acids of carbon number 20 or their esters, followed by subjecting the fraction to the column chromatography with a reversed-phase distribution system for partition refining.

2. A method of producing highly pure eicosapentaenoic acids or their esters of claim 1 wherein precision distillation is carried out under a reduced pressure of 10 Torr or below and at a temperature of 210° C. or below using three or more distillation columns.

3. A method of producing highly pure eicosapentaenoic acids or their esters of claim 1 wherein partition refining is carried out with a reversed-phase distribution column chromatography in which alkyl bond silica packing materials are charged.

4. A method of producing eicosapentaenoic acids or their esters at a purity of 99% and above, which consists of the step of subjecting a mixture of fatty acids or their esters derived from natural oils and fats to precision distillation in a plurality of distillation columns of three or more under a reduced pressure of 10 Torr or below and a temperature of 210° C. or below to obtain a fraction consisting mainly of fatty acids of a carbon number of 20 or their esters, followed by the step of subjecting the fraction to column chromatography with a reversed-phase distribution system to partition refine the fatty acids so as to separate and recover eicosapentaenoic acids or their esters from said fraction at a purity of 99% and above.

5. A method of producing eicosapentaenoic acids or their esters according to claim 4, wherein the fatty acid fraction having mainly a carbon number of 20 or their esters are partition refined by means of a reversed-phase distribution column in which electrically charged alkyl bond packing materials are employed therein.

* * * * *